United States Patent [19]

Madaus et al.

[11] 4,447,455

[45] May 8, 1984

[54] ORAL UROLITHIASIS REMEDY

[75] Inventors: Rolf Madaus, Köln-Brück; Werner Stumpf, Bensberg-Refrath, both of Fed. Rep. of Germany

[73] Assignee: Madaus and Company, Cologne, Fed. Rep. of Germany

[21] Appl. No.: 405,631

[22] Filed: Aug. 5, 1982

Related U.S. Application Data

[63] Continuation of Ser. No. 211,988, Dec. 1, 1980, abandoned, which is a continuation of Ser. No. 101,611, Dec. 10, 1979, abandoned.

[51] Int. Cl.³ ............................................. A61K 31/12
[52] U.S. Cl. .................................. 424/331; 424/157; 424/128
[58] Field of Search ....................... 424/331, 128, 157

[56] References Cited

PUBLICATIONS

Boyce et al.-J. Urologie, vol. 97, (1967), pp. 783–789.
William et al.-J. Bone Joint Surgery, vol. 46-8, (1964), pp. 493–508.
Naoki et al.-Kogyo Kagura Zasshi, vol. 60, (1957), pp. 1143–1145.
Bauer–Anat. Entwicklungsges, vol. 66, (1922), pp. 689–691.

*Primary Examiner*—Sam Rosen
*Attorney, Agent, or Firm*—Felfe & Lynch

[57] ABSTRACT

The disclosed invention deals with treating urolithiasis with alizarin. Magnesium oxide and phosphate salts may also be added.

7 Claims, No Drawings

ORAL UROLITHIASIS REMEDY

This is a continuation of Ser. No. 211,988 filed Dec. 1, 1980 which in turn was a continuation of Ser. No. 101,611 filed Dec. 10, 1979 both now abandoned.

The invention relates to an oral urolithiasis remedy, especially for the treatment and prophylaxis of illnesses due to calcium oxalate calculi and calculi containing calcium oxalate.

The chemotherapy of oxalate urolithiasis presents considerable difficulty for which no satisfactory solution was ever found. Magnesium-containing mixtures on a citrate basis are known (German Offenlegungsschrift No. 2,252,665), but their effectiveness is disputed, since the citrate content of these preparations is probably metabolized and the effectiveness of the magnesium component in this mixture is unclear with regard to the solubility ratios. Remedies containing succinimide as the active ingredient (German Patent No. 2,030,932) have never become established, and preparations based on cation exchangers provide no reliable treatment or prophylaxis. Consideration has been given to the use of complexing agents for calcium, such as glucuronic acid, or of magnesium compounds such as oxides, citrate, adipinate and nicotinate to improve the solubility of calcium oxalate, or also the use of various plant extracts containing ruberythric acid. All of these efforts have failed to produce the desired success.

It has now been found surprisingly that alizarin is suitable as a remedy for the treatment of oxalate urolithiasis patients, since it develops a decided inhibitive effect on the formation of stones, and it is also easily tolerated.

The oral urolithiasis remedy of the invention is accordingly characterized essentially by a content of alizarin, in amounts corresponding to daily doses of 140 to 500 milligrams.

It has been found that the administration of alizarin as the essential substance for the treatment of urolithiasis is decidedly effective. However, especially good results have been achieved with mixtures of alizarin and magnesium oxide together with disodium hydrogen phosphate and potassium dihydrogen phosphate. These mixtures contain potassium dihydrogen phosphate and disodium hydrogen phosphate preferably in a ratio of 5:3 by weight (potassium dihydrogen phosphate to disodium hydrogen phosphate).

Mixtures of disodium hydrogen phophate and potassium dihydrogen phosphate alone have previously been proposed and therapeutically applied for the treatment of oxalate urolithiasis patients. However, the very high phosphate dosage considered necessary for proper treatment has resulted in no more than partial success, and undesirable side-effects such as diarrhea and digestive tract disturbances are produced to a considerable extent. On the other hand, as it will be shown below, alizarin is very well tolerated and the mixture of active agents combined in accordance with the invention is likewise quite tolerable and amazingly effective.

Tests were made especially of combinations of active substances composed of approximately 5 to 14% of alizarin, 10 to 26% of magnesium oxide, 22 to 32% of disodium hydrogen phosphate and 37 to 53% of potassium dihydrogen phosphate, and particularly of a mixture in the form of dosage units containing 35 mg of alizarin, 65 mg of magnesium oxide, 150 mg of disodium hydrogen phosphate and 250 mg of potassium dihydrogen phosphate.

In addition to hard gelatine capsules and dragees, soft gelatin capsules are recommended as forms for administration. With daily doses of the special combination of active substances amounting to approximately 15 to 90 milligrams, and especially of up to about 60 milligrams, per kilogram of body weight, good success is achieved. With these especially preferred dosage units the convenient consumption of two units thrice daily will result in especially appropriate daily doses of 43 mg per kilogram of body weight.

The extraordinarily good tolerability both of alizarin itself, and of the especially desirable combination of active substances in the preferred ratios, was proved by means of the following toxicity tests:

The administration of alizarin in amounts of one gram per kilogram (in the mouse) and of up to 400 mg/kg (in the rat) was tolerated without producing symptoms. The mixture of active substances administered in the maximum applicable doses of up to 10 g/kg and 5 g/kg for the mouse and the rat, respectively, resulted in no intolerance whatsoever.

In testing the long-term toxicity in the rat, different daily doses were administered to two groups of experimental animals over a longer period of time according to the following schedule:

| Time | Daily dose Group 1 (mg/kg) | Daily dose Group 2 (mg/kg) |
| --- | --- | --- |
| First to fourth week | 200 | 600 |
| Fifth to eighth week | 250 | 750 |
| Ninth to twenty-ninth week | 300 | 1000 |

The result in Group 1 was an increase in the kidney weight in the female animals (absolutely and relatively to body weight).

In the animals of Group 2, the kidney weights of the male and female animals were increased significantly relative to body weight and to brain weight, and in the females they were increased absolutely as well. Histological examination of the kidneys provided no indication of any cause for these weight increases. It is surmised that they are to be attributed to a general hypertrophy of the paranchymal tissue of the kidney. -Histological examination of the lumbar vertebrae indicated no difference from the untreated control animals.

Testing of the long-term toxicity in the dog on the basis of the same administration schedule as in the rat gave the following result: in Group 1 the 24-hour volume of the urine was slightly increased, and the magnesium and calcium concentration in the urine was slightly lower than in the control animals. In Group 2, the magnesium and calcium concentration in the urine was lower, but the excretion of these ions was higher as was the 24-hour volume of urine. The kidney weights in the dog were also remarkably high.

In the histological study of the lumbar signal vertebrae no differences from the control animals were observed. The same applies to the EKG tests performed.

In general pharmacological tests of the active substance combination of the invention in the preferred ratios (i.e., containing 7% alizarin, 13% magnesium oxide, 30% disodium hydrogen phosphate and 50% potassium dihydrogen phosphate, hereinafter abbreviated AMDK), a study was made of the effects of the central nervous system, the smooth muscles, the coronary circulatory function, respiration and blood gases, choleresis and kidney activity; also, the anti-inflammatory action.

1. ACTION OF THE CENTRAL NERVOUS SYSTEM (a) Pentylene tetrazol convulsion test Groups of female mice of 20 to 24 grams were administered 600 and 1200 mg/kg of AMDK (per os), respectively, and pentylene tetrazol (intraperitoneal) thirty minutes afterward. The control groups received only the solvent of the AMDK. The occurrence of convulsions within ten minutes after the administration of pentylene tetrazol was noted; Table 1 shows the results:

TABLE 1

|  | N | Dose (mg/kg) p.o. | Convulsions yes N | Convulsions no N | Pentylene tetrazol action (%) |
|---|---|---|---|---|---|
| AMDK | 20 | 600 | 14 | 6 | 70 |
|  | 9 | 1200 | 8 | 1 | 88 |
| Control | 20 | — | 16 | 4 | 80 |
|  | 9 | — | 7 | 2 | 77 |

As it can be seen, the irritability of the CNS is neither increased nor decreased by AMDK.

(b) Extensive testing of the effect of AMDK (600 mg/kg, p.o.) on sleep induced by hexobarbital (100 mg/kg) in mice gave virtually no indication of any sedative action of AMDK.

(c) In the analgesia test by the focal ray method in mice, no appreciable differences from the control animals or any other manifestations were produced by 600 and 1200 mg/kg, respectively, of AMDK.

2. EFFECT ON STOMACH AND INTESTINAL ACTIVITY

The stomach and intestinal transit time was tested in the mouse to determine whether any stomach and intestinal tract effects are produced. No effect was observed on the rate of stomach and intestinal passage in comparison with the controls.

Intestinal motility was also tested in the mouse. After the oral administration of 600 mg/kg of AMDK to the animals of the test group and 25 ml/kg of tragacanth to those of the control group, these completely fasting mice were given 100 micrograms per kg of Doryl$^{(R)}$ as a motility stimulating agent, and immediately thereafter a mixture of tragacanth and carmine red (50 ml/kg, p.o.). After another 25 minutes the mice were killed and the length of the intestine from the pylorus to the anus and the length dyed with carmine red were measured. Table 2 shows the result: AMDK has virtually no effect on intestinal motility.

TABLE 2

Intestinal motility in male mice
(Dye migration length: total length of intestine in %)

| Substance | N | Dosage | Effect % | Effect compared with control (%) |
|---|---|---|---|---|
| AMDK | 10 | 600 mg/kg | 66.63 ± 12.82 | +19.61 |
| Tragacanth | 10 | 25 ml/kg | 63.12 ± 8.7 |  |

3. ACTION ON THE HEART AND CIRCULATORY SYSTEM, RESPIRATION AND BLOOD GASES

The performance of the heart and circulatory functions and of the blood gases was analyzed in dogs and rats. The parameters were pulse rate, blood pressure in the left ventricle, blood pressure in the right auricle, blood pressure in the femoral artery, respiration rate, respiratory volume, blood gases and pH. The AMDK dosage in the dogs was 600 mg/kg, and 300 and 600 mg/kg in the rats.

Neither in the rat nor in the dog were significant changes found in the parameters, so that no side-effects in the heart and circulatory and respiratory systems are to be anticipated.

4. ACTION ON CHOLERESIS

To obtain an idea of the secretory action of the mixture of the invention, the effect of AMDK on th biliary secretion of the liver in the rat was studied with doses of 600 mg of AMDK per kilogram of body weight. Table 3 shows the result, namely that bile secretion is virtually unaltered.

TABLE 3

Effect of 600 mg/kg AMDK intraduodenal on choleresis in the narcotized rat.

|  | N | Bile secretion in ml/100 g/30 min |
|---|---|---|
| AMDK | 10 | 0.22 ± 0.014* |
| Control (tragacanth) | 10 | 0.23 ± 0.012* |

*Average error

5. ACTION OF THE KIDNEYS (a) Testing of the effect of AMDK on urinary excretion and concentration and excretion of $Na^+$, $K^+$, $Cl^-$ and creatinine in waking rats.

After oral administration of AMDK the previously fasting rats were placed overnight (16 hours) in diuresis cages and the urine was collected commonly in funnels. During this period the animals were in an air-conditioned room of a temperature of $+26°$ C. and an atmospheric humidity of 60%. At the end of the experiment, the following parameters were determined in the combined urine of each animal: urinary excretion (computed per hour and per kilogram of body weight), $Na^+$ and $K^+$ concentration (flame photometry) and $Cl^-$ concentration (coulometry). The determination of creatinine was performed on the basis of Boehringer's "Biochemica-Test-Kombination" No. 15943. The amounts secreted were computed from the measured concentrations and volumes of the urine (see Table 4).

(b) Determination of urinary excretion, GFR, fractional liquid resorption, and of the fractional resorption and clearances for $Na^+$, $K^+$, $Cl^-$, urea, PAH and glucose.

These determinations were performed in mannitol diuresis on narcotized male rats (fasting) over a period of about three hours.

After the depth of narcosis was sufficient, both ureters were cannulated. Intravenous injections and infusions were performed through a jugular vein, and the blood sampling from a carotid artery. The preliminary injection of inulin (50 mg/kg) and PAH (20 mg/kg) was performed 20 minutes before the infusion began. The AMDK (800 mg/kg) was placed in the duodenum behind the pylorus at the time the infusion was started. The control animals received a suspension of tragacanth in water intraduodenally in the same manner. The volume infused was 0.2 ml per minute per animal. Inulin was infused at a rate of 5 mg/kg per minute, and PAH at 0.2 mg/kg per minute. The infusion medium was a 5% solution of mannitol and Ringer's mixture. Urine was collected one hour and two hours after the beginning of the infusion, for seven minutes, during which time about 2 ml of blood was taken from the carotid artery.

Carbon 14-tagged inulin (1 mC/392 mg), mixed with inactive inulin in a ratio of 1:100, was added in the form of a 2% solution to the required amounts of the pre-injection solution and the infusion solution. The radioactivity was measured in a liquid scintillation counter. $Na^+$ and $K^+$ were determined by flame photometry and $Cl^-$ by coulometry. The urea determination was performed by the urea method (Boehringer Biochemica No. 15945). PAH was determined by the method of A. C. Bratton and E. K. Marshall, Jr. (J. Biol. Chem. (Am.) 128 (1939) 537). Glucose was determined by the GOD-Perid method (Boehringer Biochemica No. 15755). The values of the fractional resorption and the values given on the clearances are averages from both periods of urine collection and the corresponding blood samples. The results are summed up in Table 5.

TABLE 4

| Diuresis test using female rats (ten) of 200 to 250 grams after the oral administration of 600 mg/kg of AMDK | | |
|---|---|---|
| Uresis (g urine/h × kg) | AMDK 2.03 ± 0.38 | Controls 2.26 ± 0.48 |
| $Na^+$ | | |
| Concentration (millimoles/liter) | 76.5 ± 9.52* | 26.4 ± 8.3 |
| Excretion (micromoles/h/kg) | 155.9 ± 39.1* | 59.5 ± 20.1 |
| $K^+$ | | |
| Concentration (millimoles/liter) | 176.4 ± 40.9* | 101.6 ± 22.4 |
| Excretion (micromoles/h/kg) | 348.6 ± 47.6* | 234.6 ± 93.7 |
| $Cl^-$ | | |
| Concentration (millimoles/liter) | 47.7 ± 12.5 | 41.6 ± 6.4 |
| Excretion (micromoles/h/kg) | 95.6 ± 26.4 | 95.2 ± 28.9 |
| Creatinine | | |
| Concentration (milligrams/100 ml) | 122.3 ± 40.7* | 72.9 ± 10.0 |
| Excretion | 2.43 ± 0.29* | 1.64 ± 0.31 |

*A significant difference ($\alpha = 0.01$)

TABLE 5

| Clearance test on male rats of 250–370 g (20 test animals, 20 controls) after oral administration of 800 mg/kg. | | |
|---|---|---|
| | AMDK | Controls |
| Uresis (ml/min/kg) | 0.604 ± 0.124 | 0.760 ± 0.142 |
| GFR (ml/min/kg) | 9.39 ± 1.98 | 10.23 ± 1.96 |
| Resorbed fluid | 93.38 ± 1.64 | 92.48 ± 1.28 |
| $Na^+$ Resorbed (% of filtered fluid) | 95.02 ± 2.12 | 93.83 ± 1.37 |
| Clearance (ml/min/kg) | 0.456 ± 0.187 | 0.632 ± 0.137 |
| $K^+$ Resorbed (% of filtered fluid) | 39.35 ± 15.24 | 53.44 ± 6.21 |
| Clearance (ml/min/kg) | 5.97 ± 1.63 | 4.77 ± 0.98 |
| $Cl^-$ Resorbed | 92.75 ± 2.46 | 91.48 ± 1.75 |
| (% of filtered fluid) | | |
| Clearance (ml/min/kg) | 0.664 ± 0.212 | 0.872 ± 0.226 |
| Urea, clearance (ml/min/kg) | 7.12 ± 1.36 | 9.12 ± 1.58 |
| PAH Excreted (micrograms per minute per kilogram) | 95.08 ± 23.73 | 84.45 ± 47.88 |
| Clearance (ml/min/kg) | 27.49 + 5.58 | 24.73 ± 7.57 |

Results of the excretory tests:
(a) The experimental animals excrete a urine—not increased in rate—which, with regard to the concentration and excretion of $Na^+$, $K^+$ and creatinine, is greater than that of the controls. In addition, the higher concentration and excretion of $Na^+$ and $K^+$ is easily understandable: it is the consequence of the fact that considerable amounts of $Na^+$ and $K^+$ are administered with the test substance. The higher creatinine concentration in the urine of the experimental animals is probably the consequence of the higher total concentration of the urine. Although this was not measured, the fact of a higher $Na^+$ and $K^+$ concentration together with an unchanged $Cl^-$ concentration points to a higher total concentration. This then expresses itself in the higher creatinine concentration.
(b) In none of the measured parameters is there a significant difference between the experimental and control groups. In contrast to Experimental Series (a), the amount of $Na^+$ and $K^+$ administered does not change as a result of the unequally higher uresis. From this, and from the fact that there is no difference whatever between the experimental groups and the control groups, it follows that the effects observed in Experimental Series (a) are exclusively the consequence of the administration of AMDK.

In other words, AMDK, in a single enteral administration, does not affect kidney function. Changes in the concentration and uresis of $Na^+$ and $K^+$ under the conditions of the diuresis test on waking rats are the consequence of the high input of these ions. They cannot be related to any influence on kidney function.

6. ANTI-INFLAMMATORY ACTION

The possibility of any effect on inflammatory reactions was tested on edema of the paws of rats (groups of ten rats each) induced by viscarin-carrageenin. The AMDK dose was 600 mg/kg (p.o.). The AMDK was administered 2 hours after the edematization. The measurement of the course of the edema was performed at 3, 5, 7 and 24 hours after the edematization. The results were examined by the F test and the t test for similarity of the variance of the experimental and control groups and for significant difference between the averages of both groups. Where the variances between the experimental and control groups were unequal, the more rigorous t test (according to SNEDECOR) was applied for the judgment. Table 6 summarizes the results.

TABLE 6

| | | | | |
|---|---|---|---|---|
| Controls - 10 animals | | | | |
| Edema volume x̄ [ml] | 79.4 | 80.7 | 76.5 | 25.2 |
| ± s | 12.9 | 12.1 | 13.1 | 10.6 |
| AMDK - 10 animals | | | | |
| Edema volume x̄ [ml] | 71.5 | 71.9 | 68.9 | 24.2 |
| ± s | 15.9 | 13.5 | 12.4 | 10.1 |
| Percentage of inhibition | 9.95 | 10.9 | 9.93 | 3.97 |
| Sodium escinate* - 10 animals | | | | |
| Edema volume x̄ [ml] | 46.5 | 50.7 | 46.6 | 14.9 |
| ± s | 11.5 | 10.8 | 12.9 | 8.5 |
| Percentage of inhibition | 41.4 | 37.2 | 39.1 | 40.9 |

The course of the edema is found to be slightly inhibited by the presence of AMDK.
*[TRANSLATOR'S NOTE: Literal interpretation of Na-Aescinat. I am not aware of the existence of such a term in German or English.]

The results reported above indicate on the whole that the combination, in accordance with the invention, of alizarin, magnesium oxide, disodium hydrogen phosphate and potassium phasphate has no detrimental effect on the activity of the stomach and intestine, and that it is excreted mainly through the kidneys, where in combination with an influence on the urinary system it exercises a surprisingly favorable and previously unachieved action against inflammatory processes, while the rather inhibiting action against inflammatory processes will be helpful in the treatment of urolithiasis.

To sum up, therefore, it can be stated that the mixture of substances pursuant to the invention, and especially its alizarin component, has proven to be extremely well tolerated in the acute toxicity test. In none of the tests performed were there any indications of the intolerability or side-effects that were to be expected. The only slight side-effect that could be determined (a slight bronchospasm) is probably of no practical significance in view of the tremendous difference between the chosen human daily dose and the dose used in the animal experiment.

The above results clearly show that the preparations in accordance with the invention can be administered without harm even for long periods of time.

For the testing of the possible therapeutic effects, the individual components were first tested in vitro, with the following findings:
(1) The alizarin was found to have an inhibiting action on the crystallization of calcium oxalate;
(2) The presence of magnesium salts brought about a definite increase in the solubility of calcium oxalate;
(3) The phosphate mixture on the one hand stabilizes the pH tending to increase the excretion of citrate, favoring the formation of calcium chelates in the urine, and on the other hand it acts as a growth inhibitor with regard to calcium oxalate crystallization.

CLINICAL FINDINGS 22 patients (oxalate-calculogenetic) were subjected for 1 to 6 years to treatment to inhibit calculogenesis based on an average of two of the capsules described in Example 2, thrice daily. Eighteen of the patients were classified as rapidly recidivitive oxalate-calculogenetic (developing at least 4 stones per year), while the remaining four patients manifested recidivitive oxalate-calculogenesis amounting to less than 4 stones per year.

In all cases, calculogenesis was reliably prevented, regardless of the presence or absence of hypercalciuria. Tolerance was generally very good. Observation of the patients by common laboratory testing (blood tests etc.) indicated no deviation from the norm.

The following examples show the preparation of a number of different medication forms:

EXAMPLE 1

Preparation of hard gelatine capsules

For a batch of 1000 size 0 capsules, the following components were weighed out:

| | |
|---|---|
| Alizarin | 35.0 g |
| Magnesium oxide | 65.0 g |
| Disodium hydrogen phosphate, anhydrous | 150.0 g |
| Potassium dihydrogen phosphate, anhydrous | 250.0 g |
| Carboxymethylcellulose | 2.0 g |
| Magnesium stearate | 3.0 g |

Method of preparation

The carboxymethylcellulose was dissolved by stirring in a mixture of methanol and methylene chloride. This solution was used in an amount sufficient for making a dough of the active ingredients which had first been thoroughly mixed separately. The moist mass was forced through a V₂A sieve of 2 mm mesh size and then dried at 40°–50° C.

The dry granulate was crushed through a V₂A sieve of 0.8 mm mesh size and then the magnesium stearate was mixed in.

The finished composition was packed in amounts of 505 mg in size 0 hard gelatine capsules by means of a capsule filling machine.

EXAMPLE 2

Preparation of soft gelatine capsules

For a batch of 1000 capsules in the 11 minim oblong size, the following components were weighed out:

| | |
|---|---|
| Alizarin | 35.0 g |
| Magnesium oxide | 65.0 g |
| Disodium hydrogen phosphate, anhydrous | 150.0 g |
| Potassium dihydrogen Phosphate, anhydrous | 250.0 g |

Method of Preparation

The active substances were finely ground in a ball mill.

The ground material was stirred with a sufficient amount of an indifferent oil (e.g., paraffin oil of high fluidity) to form a paste.

The paste was then loaded by means of a suitable encapsulation apparatus into soft gelatine capsules of the 11 minim oblong format.

EXAMPLE 3

Preparation of Dragees

For a batch of 1000 dragees the following components were weighed out:

| | |
|---|---|
| Alizarin | 35.0 g |
| Magnesium oxide | 65.0 g |
| Disodium hydrogen phosphate, anhydrous | 150.0 g |
| Microcrystalline cellulose | 40.0 g |

| | |
|---|---|
| Carboxymethylcellulose | 5.0 g |
| Wheat starch | 20.0 g |
| silicon dioxide, highly disperse | 5.0 g |
| Magnesium stearate | 5.0 g |

Method of Preparation

The active substances were finely ground in a ball mill and then mixed with the microcrystalline cellulose.

The binding agent (carboxymethylcellulose) was dissolved by stirring in a mixture of methanol and methylene chloride. Then the above powder mixture was made into a dough with this solution and pregranulated through a $V_2A$ sieve of a mesh size of 2 mm.

After drying at 40°–50° C., the coarse granulate was crushed by forcing through a sieve of 1.0 mm mesh size. Then the adjuvants wheat starch, silicon dioxide and magnesium stearate were mixed in.

The pressing composition thus prepared was pressed in a tableting press to biconvex dragee tablets of 11 mm diameter weighing 575 mg each.

The tablets were candy-coated in a known manner with sugar solutions in which generally common adjuvants such as calcium carbonate, titanium dioxide and talc were suspended, to yield dragees weighing 950 mg each.

We claim:

1. A composition for the treatment of urolithiasis comprising effective amounts of
   alizarin,
   magnesium oxide,
   disodium hydrogen phosphate, and
   potassium hydrogen phosphate.

2. Composition as claimed in claim 1 comprising

| | |
|---|---|
| 5 to 14% | alizarin, |
| 10 to 26% | magnesium oxide, |
| 22 to 32% | disodium hydrogen phosphate, and |
| 37 to 53% | potassium dihydrogen phosphate. |

3. Composition as claimed in claim 1 in unit dosage form containing

| | |
|---|---|
| 35 mg | alizarin, |
| 65 mg | magnesium oxide, |
| 150 mg | disodium hydrogen phosphate, and |
| 250 mg | potassium dihydrogen phosphate. |

4. Method of treating urolithiasis, which method comprises administering to an afflicted subject a therapeutically effective amount of alizarin.

5. Method as claimed in claim 4 wherein a daily dosage of 140 to 500 mg is administered to the afflicted subject.

6. Method as claimed in claim 4 wherein an alizarin-containing composition is administered also containing magnesium oxide, disodium hydrogen phosphate and potassium dihydrogen phosphate.

7. Method as claimed in claim 6 wherein an alizarin-containing composition is administered containing

| | |
|---|---|
| 10 to 26% | magnesium oxide |
| 22 to 32% | disodium hydrogen phosphate, and |
| 37 to 53% | potassium dihydrogen phosphate. |

* * * * *